(12) United States Patent
Ho et al.

(10) Patent No.: US 7,998,162 B2
(45) Date of Patent: Aug. 16, 2011

(54) SYSTEM AND METHOD FOR EMBOLIC PROTECTION

(76) Inventors: Pei Ho, Hong Kong SAR (CN); Ronald L. Dalman, Portola Valley, CA (US)

( * ) Notice: Subject to any disclaimer, the term of this patent is extended or adjusted under 35 U.S.C. 154(b) by 611 days.

(21) Appl. No.: 12/075,117

(22) Filed: Mar. 5, 2008

(65) Prior Publication Data

US 2008/0243168 A1   Oct. 2, 2008

Related U.S. Application Data

(60) Provisional application No. 60/905,268, filed on Mar. 5, 2007.

(51) Int. Cl.
*A61M 29/00* (2006.01)
(52) U.S. Cl. ..................................................... 606/194
(58) Field of Classification Search .................. 606/194, 606/192, 193, 195; 623/1.11, 1.3, 1.13; 604/509, 604/95.03, 101.01–101.05, 103, 103.05, 604/103.07, 103.04; 128/207.15
See application file for complete search history.

(56) References Cited

U.S. PATENT DOCUMENTS

| | | | |
|---|---|---|---|
| 4,548,597 A | 10/1985 | Nelson | |
| 5,588,424 A * | 12/1996 | Insler et al. | 128/207.15 |
| 5,755,773 A | 5/1998 | Evans et al. | |
| 6,290,710 B1 | 9/2001 | Cryer et al. | |
| 6,443,156 B1 * | 9/2002 | Niklason et al. | 128/207.14 |
| 6,540,722 B1 | 4/2003 | Boyle et al. | |
| 6,592,548 B2 * | 7/2003 | Jayaraman | 604/103.04 |
| 6,969,381 B2 | 11/2005 | Voorhees | |
| 2002/0120226 A1 | 8/2002 | Beck | |
| 2006/0079859 A1 | 4/2006 | Elkins et al. | |
| 2006/0149214 A1 | 7/2006 | Breiter et al. | |

* cited by examiner

*Primary Examiner* — Anhtuan Nguyen
*Assistant Examiner* — Amy Lang
(74) *Attorney, Agent, or Firm* — Lumen Patent Firm

(57) ABSTRACT

A balloon catheter system distinguishing a proximal balloon catheter system and a distal balloon catheter is provided. The proximal balloon catheter system has a first and a second catheter. These two catheters are positioned side-by-side over at least part of the longitudinal area of their outer surfaces, and they are detachably connected to each other. A first inflatable member is attached to the first catheter near the distal end of the first catheter. The distal balloon catheter distinguishes a catheter part with a distal end and a proximal end, and an exchange rod attached near the proximal end of the catheter part. The catheter part has a second inflatable member encircling the outer surface of the catheter part. The balloon catheter system can be used for example in methods of isolating a segment of a vessel, generating reversal fluid flow and creating an in-vivo shunt with a balloon catheter.

4 Claims, 17 Drawing Sheets

SYSTEM AND METHOD FOR EMBOLIC PROTECTION

CROSS-REFERENCE TO RELATED APPLICATIONS

This application claims priority from U.S. Provisional Application No. 60/905,268, filed on Mar. 5, 2007, which is incorporated herein by reference.

FIELD OF THE INVENTION

The present invention relates generally to vascular medicine. More particularly, the present invention relates to a system and method for embolic protection.

BACKGROUND OF THE INVENTION

There are a number of systems and methods available for embolic protection during carotid artery stenting (CAS) procedures. However, these systems and methods have a number of drawbacks. In one method, filters are used to capture emboli during the CAS procedure. However, filters fail to capture all emboli, such that emboli may pass to the brain and cause stroke. In another method, a distal occlusion balloon is used during the CAS procedure. A problem with this method, however, is that it stops internal carotid artery (ICA) blood flow to the brain, which causes cerebral ischemia in a certain percentage of patients. In addition, distal occlusion balloons also fail to capture all emboli. A third method uses a proximal occlusion balloon plus an external carotid artery (ECA) balloon. This method maintains a reversal flow throughout the procedure, and thus diminishes blood flow to the brain. Thus, there is a need in the art to develop new methods and systems that would at least overcome some of these disadvantages. The present invention addresses these needs.

SUMMARY OF THE INVENTION

A balloon catheter system distinguishing two parts is provided. The first part is a proximal balloon catheter system and the second part is a distal balloon catheter. The proximal balloon catheter system has a first and a second catheter. These two catheters are positioned side-by-side over at least part of the longitudinal area of their outer surfaces, and they are detachably connected to each other. During a procedure, the second catheter can be detached from the first catheter and subsequently removed from the catheter system. A first inflatable member is attached to the first catheter near the distal end of the first catheter. When the first and second catheters are positioned side-by-side, the first inflatable member encircles the outer diameters of the first and second catheters.

The distal balloon catheter distinguishes a catheter part with a distal end and a proximal end, and an exchange rod attached to the proximal end of the catheter part. The catheter part has attached thereto near its distal end a second inflatable member that encircles the outer diameter of the catheter part. According to one embodiment of the invention, at least the distal part of the distal balloon catheter can pass through the lumen of the second catheter of the proximal balloon catheter system. The position of the distal part of the distal balloon catheter can be adjusted by moving the exchange rod which subsequently positions the second inflatable member with respect to the first inflatable member in a vessel. The distal end of the catheter part of the distal balloon catheter has a conical tip of elastic material expandable under fluid or blood pressure.

The balloon catheter system can be used for example in methods of isolating a segment of a vessel, generating reversal fluid flow and creating an in-vivo shunt with a balloon catheter. In these methods a proximal part of a vessel can be occluded with the first inflatable member of the proximal balloon catheter system. A distal part of a vessel can be occluded with the second inflatable member of the distal balloon catheter. Once first and second inflatable members are inflated and isolate a vessel segment, the distal balloon catheter is capable of acting as an in-vivo shunt to maintain blood flow from proximal of the first inflatable member to distal of the second inflatable member through the catheter part of the distal balloon catheter. Furthermore, fluid inside the vessel segment between the first and second inflated members could flow into the distal lumen end of the first catheter when the first and second inflatable members are inflated, and exit at the proximal end of the lumen of the first catheter.

The advantage of the embolic protection system and method is that no crossing of a lesion with guidewire occurs before protection is established, theoretically leading to fewer missed emboli. In addition, this method involves only a very short period of reversal flow of the target vessel, for crossing the lesion, before the distal occlusion balloon is inflated. Blood flow in the target vessel may be quickly re-established through the in-vivo shunt once the distal occlusion balloon (i.e. second inflatable member) is inflated. In addition, after angioplasty and stenting is completed, reversal flow and aspiration can remove debris floating between the distal (second) and proximal (first) occlusion balloons.

In the case where the artery is the common carotid artery (CCA) and the target vessel is the internal carotid artery (ICA), there are a number of additional advantages. With the presence of forward flow of blood in the ICA, even with the presence of ICA-ECA collaterals, the flow in the external carotid artery (ECA) will be retrograde during the CAS procedure. Thus small particles will not flow back into cerebral circulation via ECA collaterals during the procedure. In addition, even if a small amount of debris remains in the carotid bifurcation after carotid angioplasty and stenting, after deflation of the ICA balloon, the pressure gradient will cause blood to flow into the ECA and the first catheter of the proximal balloon catheter system, further decreasing the risk of emboli flow to the ICA, and hence the brain. Other advantages include the ability to overcome the tortuous distal ICA restriction, and occluded or excessively dilated ECA will not be a restriction for usage of this embolic protection device.

BRIEF DESCRIPTION OF THE FIGURES

The present invention together with its objectives and advantages will be understood by reading the following description in conjunction with the drawings, in which.

DETAILED DESCRIPTION

The present invention is a system and method for emboli protection during angioplasty and stenting of a stenotic arterial lesion. According to the method, an inflow artery is first occluded with a proximal occlusion balloon catheter. This occlusion causes a temporary reversal of blood flow in the artery, which allows passage of a distal occlusion balloon catheter into the target vessel. Upon inflation of both the proximal and distal balloons, the segment of diseased vessel will be isolated. Any debris and blood inside the segment of vessel will flow out through the proximal balloon catheter. Subsequently, an in-vivo shunt can be established to allow blood to flow forward from the inflow artery proximal to the proximal occlusion balloon to the target vessel distal to the distal occlusion balloon. Accordingly, blood supply to an organ supplied by the target vessel can be maintained during the majority of the time of the angioplasty and stenting procedure.

Figure 1:
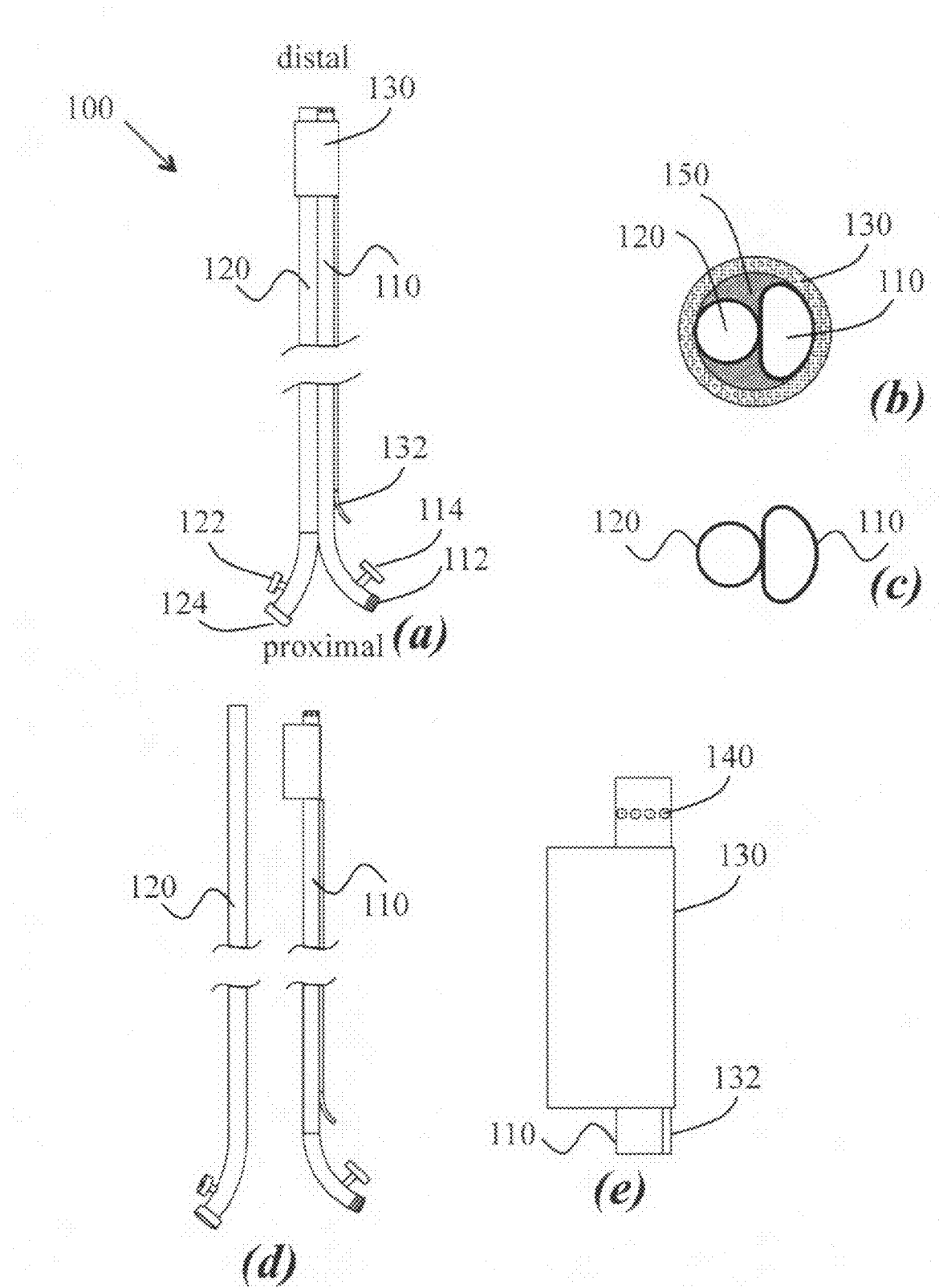
FIG. 1 shows according to embodiments of the present invention (a) a proximal balloon catheter system, (b) a cross-section of the proximal balloon catheter system through first inflatable member 130, (c) a cross section of first and second catheters, (d) first and second catheter detached from each other, and (e) a close-up of the first catheter with the first inflatable member attached to the first catheter and the second catheter removed.
Figure 2:
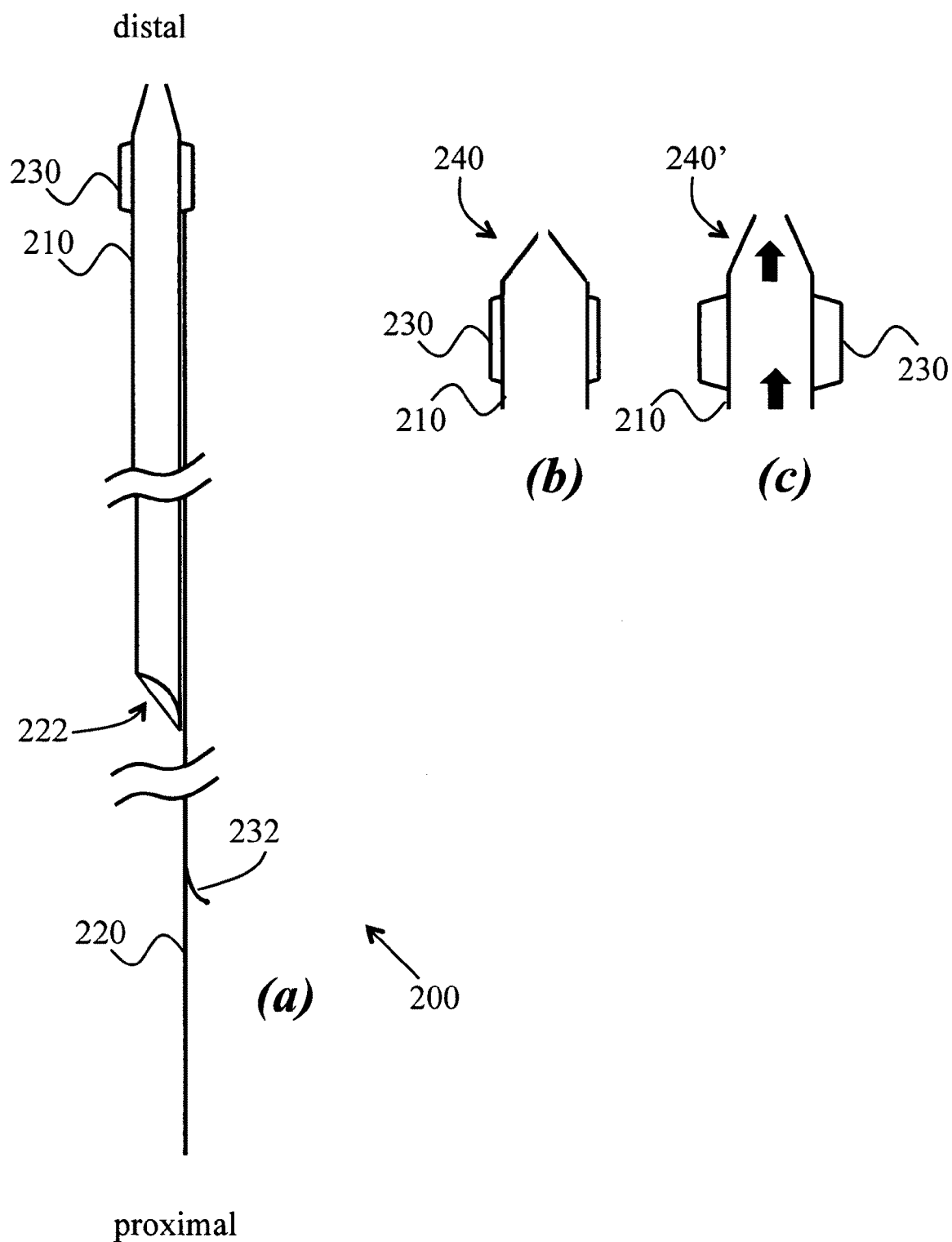
FIG. 2 shows according to an embodiment of the present invention (a) a distal balloon catheter, (b) a close-up of the distal end of the distal balloon catheter, and (c) opening up of the tip of the distal end of the distal balloon catheter under fluid or blood pressure.

The balloon catheter system includes proximal balloon catheter system 100 with a first catheter 110 and a second catheter 120 (FIG. 1) and a distal balloon catheter 200 (FIG. 2). The first and second catheters 110, 120 are positioned side-by-side over at least part of their longitudinal area of their outer surfaces. The second catheter is surrounded but not attached by a thin layer of compressible material 150 over its distal part for a short segment longitudinally. The second catheter 120 can be detached from the first catheter 120 during a procedure as shown in FIG. 1d and subsequently removed from the proximal balloon catheter system 100. In one example, the attachment location can be distal to the Y-shape as shown in FIG. 1a. In general, the first and second catheters 110, 120 attach over their proximal ends when positioned side-by-side. In one embodiment, first catheter 110 has a larger diameter than second catheter 120. In another embodiment, the distal end of the first catheter 110 has sideholes 140 that facilitate aspiration of blood and debris.

A first inflatable member 130 (inflatable via 132 using fluid or air) is attached to the first catheter 110 near the distal end of the first catheter 110. When the first and second catheters 110, 120 are positioned side-by-side the first inflatable member 130 encircles the outer diameters of both catheters 110, 120.

The proximal outlets of the first and second catheters 110, 120 when positioned side-by-side can be Y shaped (FIG. 1a). One end 112 of the Y outlet of first catheter 110 can be connected to tubing and then to a filter device and a venous catheter. The other end 114 of the Y outlet of first catheter 110 allows for syringe aspiration. One end 122 of the Y outlet of second catheter 120 allows for syringe aspiration and the other end 124 allows for passage of the distal balloon catheter 200 over a guidewire.

Distal balloon catheter 200 distinguishes a catheter part 210 with a distal end and a proximal end (e.g. 90-150 mm in length) and an exchange rod 220 attached to the proximal end of catheter part 210. The catheter part 210 has attached thereto near its distal end a second inflatable member 230 (inflatable via 232) that encircles the outer diameter of the catheter part 210 of distal balloon catheter 200. The position of distal part 210 with respect to the first catheter 110 can be adjusted by moving the distal balloon catheter 200 through the lumen of second catheter 120 or by moving it along a (partial) enclosure with respect to first catheter (see 1710 in FIGS. 17 and 18). Accordingly, catheter part 210 of distal balloon catheter 200 is capable of acting as in-vivo shunt to maintain blood flow from proximal of the first inflatable member 130 to organ(s) distal to second inflatable member 230 through catheter part 210 of distal balloon catheter system 200. In one embodiment, the proximal opening of catheter part 210 has a tapered shape 222.

The tip of the catheter part 210 of distal balloon catheter 200 has a conical shape 240 with elastic material, and can expand (240') when the pressure of fluid flow (e.g. systolic blood flow) inside it increases (FIG. 2b,c).

Figure 3:
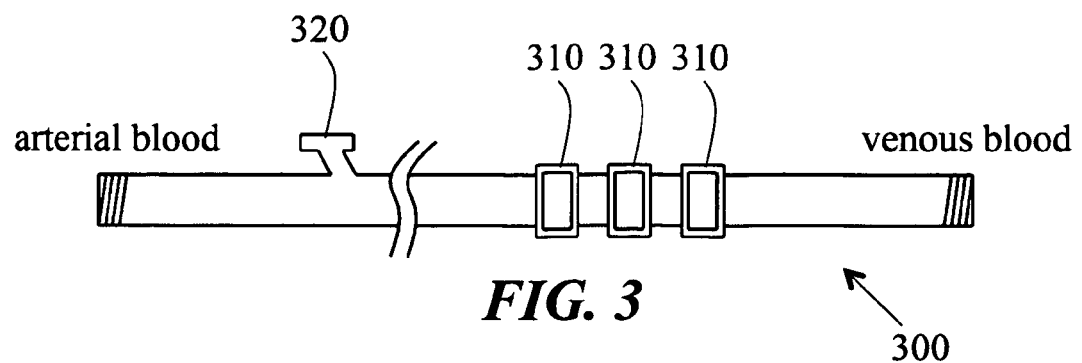
FIG. 3 shows a filter mechanism according to an embodiment of the present invention.

FIG. 3 shows a blood filtering device 300 (outside the body) to filter out debris in the outflow blood back to the human circulation. The filter with three layers of filters 310 with predetermined pore sizes. The filters to filter out debris in the outflow blood back to the human circulation 310 can be removed during the procedure if they are thrombosed by debris. This procedure can take place with only a small amount of blood loss. Side port 320 can be used for aspiration of blood during change of filter if necessary.

Figure 4:
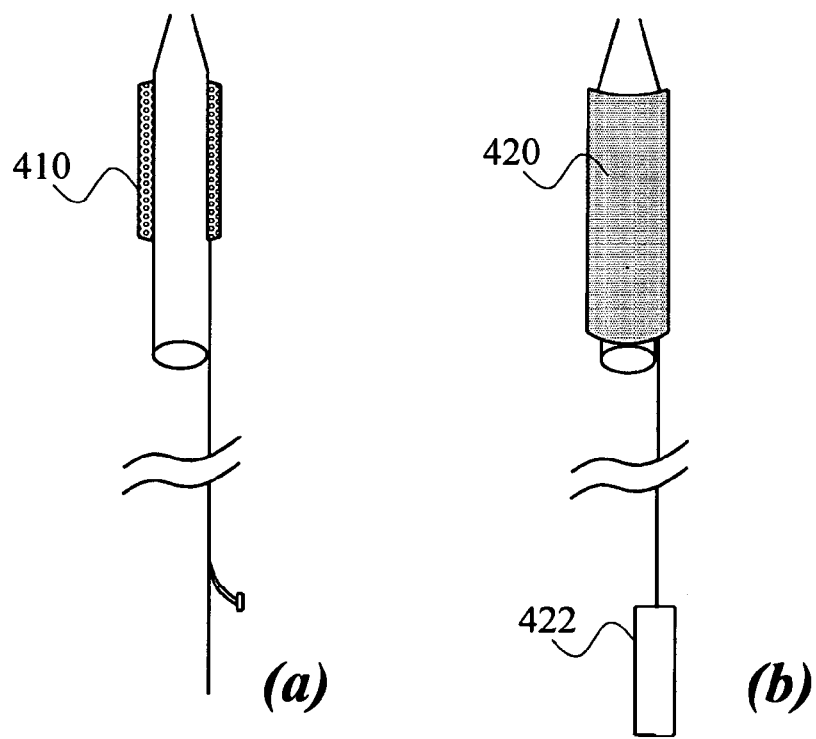
FIG. 4 shows according to embodiments of the present invention a (a) an angioplasty balloon 410 and (b) a stent 420 that can pass up and over the distal balloon catheter below its inflatable member.

FIG. 4 shows an angioplasty balloon 410 and a stent 420. The distal part of the angioplasty balloon and stent with a catheter inside for support and can slide over the distal balloon catheter to a position below the second inflatable member and the proximal part is a support rod and inflation port. A deployment handle 422 can be used to maneuver stent 420.

In general, the balloon catheter system of this invention can be used with any artery and target vessel. The following description is an example according to an embodiment of the invention of the use of the balloon catheter system where the artery is the common carotid artery (CCA) and the target vessel is the internal carotid artery (ICA).

Figure 5:
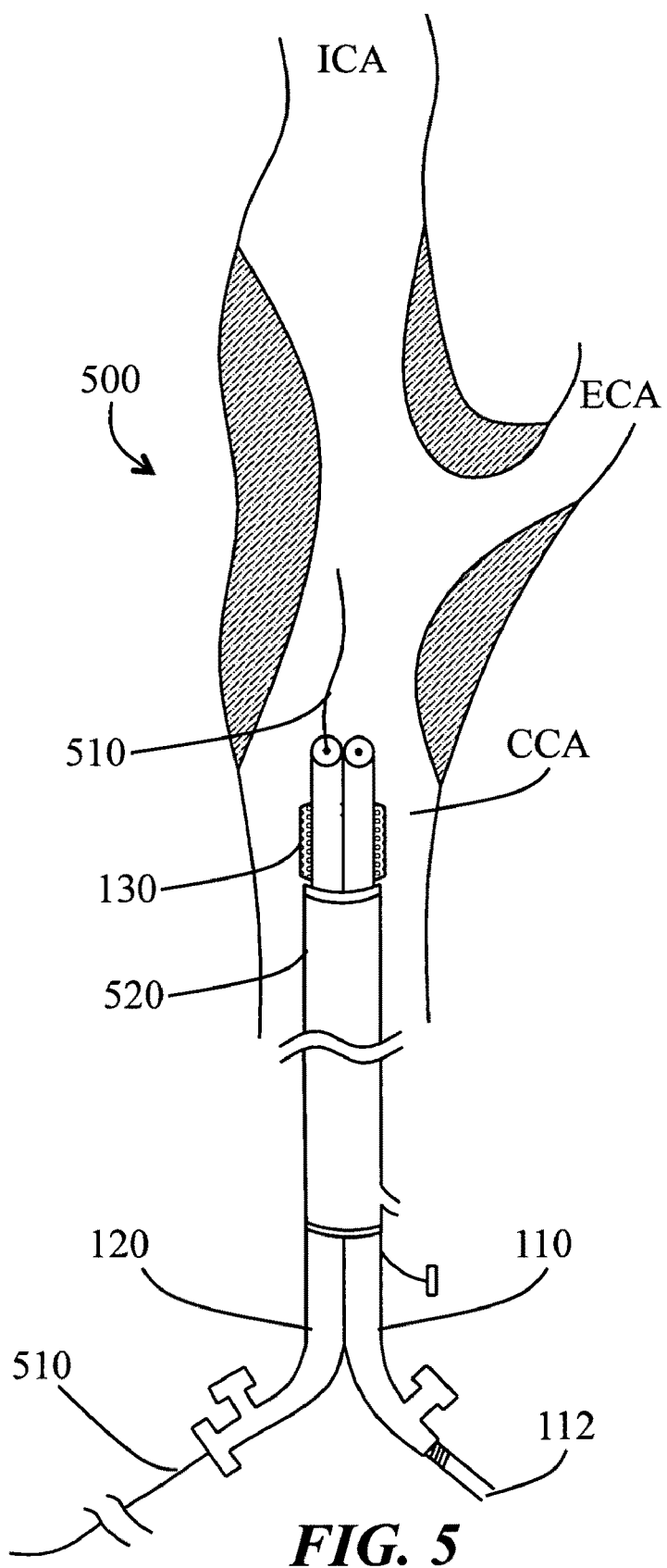
FIGS. 5-16 show method steps according to embodiments of the present invention.

FIG. 5 shows an example of a stenotic lesion present over the carotid artery bifurcation 500 extending into the proximal internal carotid artery (ICA) and the proximal external carotid artery (ECA). A guidewire 510 (e.g. 0.035" in diameter) is passed to the common carotid artery (CCA) or ECA as necessary, followed by parking of a guiding sheath 520 over the CCA. The proximal balloon catheter system is passed over guidewire 510 inside guiding sheath 520 to a position proximal to the stenotic lesion.

Figure 6:
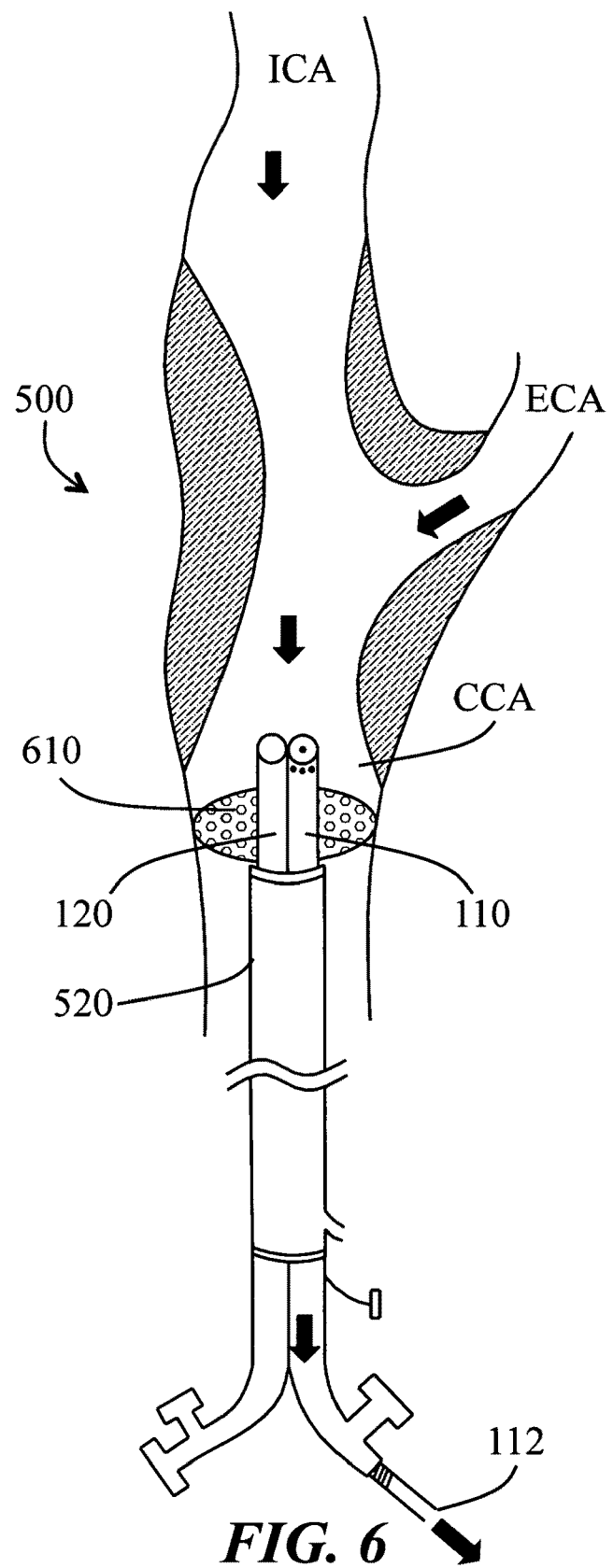
Figure 7:
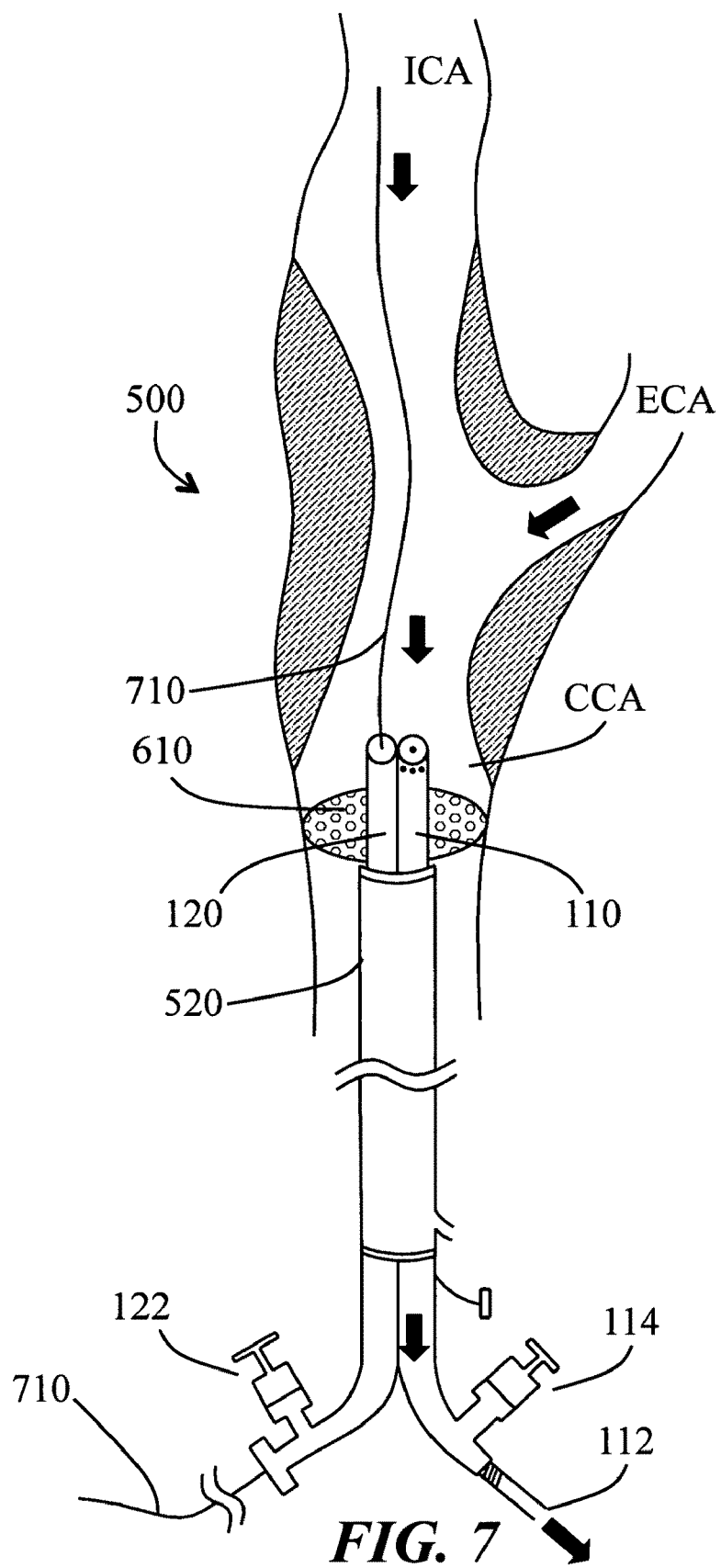

Following the exemplary procedure according to an embodiment of the invention, guidewire 510 is removed (FIG. 6). Outlet 112 of first catheter 110 is then connected first to tubing, then to a blood-filtering device, and finally to a venous catheter. The first inflatable member 130 of first catheter 110 is inflated 610 to occlude forward blood flow into the CCA, whereby retrograde flow of blood from both the ECA and the ICA is established as shown by the arrows in FIG. 6.

A guidewire 710 (e.g. 0.014" in diameter) is passed through second catheter 120 and crosses the stenotic lesion 500. During this process, retrograde flow of blood from the ICA and ECA can be further enhanced with syringe aspiration from first catheter 110 at output port 114. Additional aspiration can be applied at output port 122 of second catheter 120.

Figure 8:
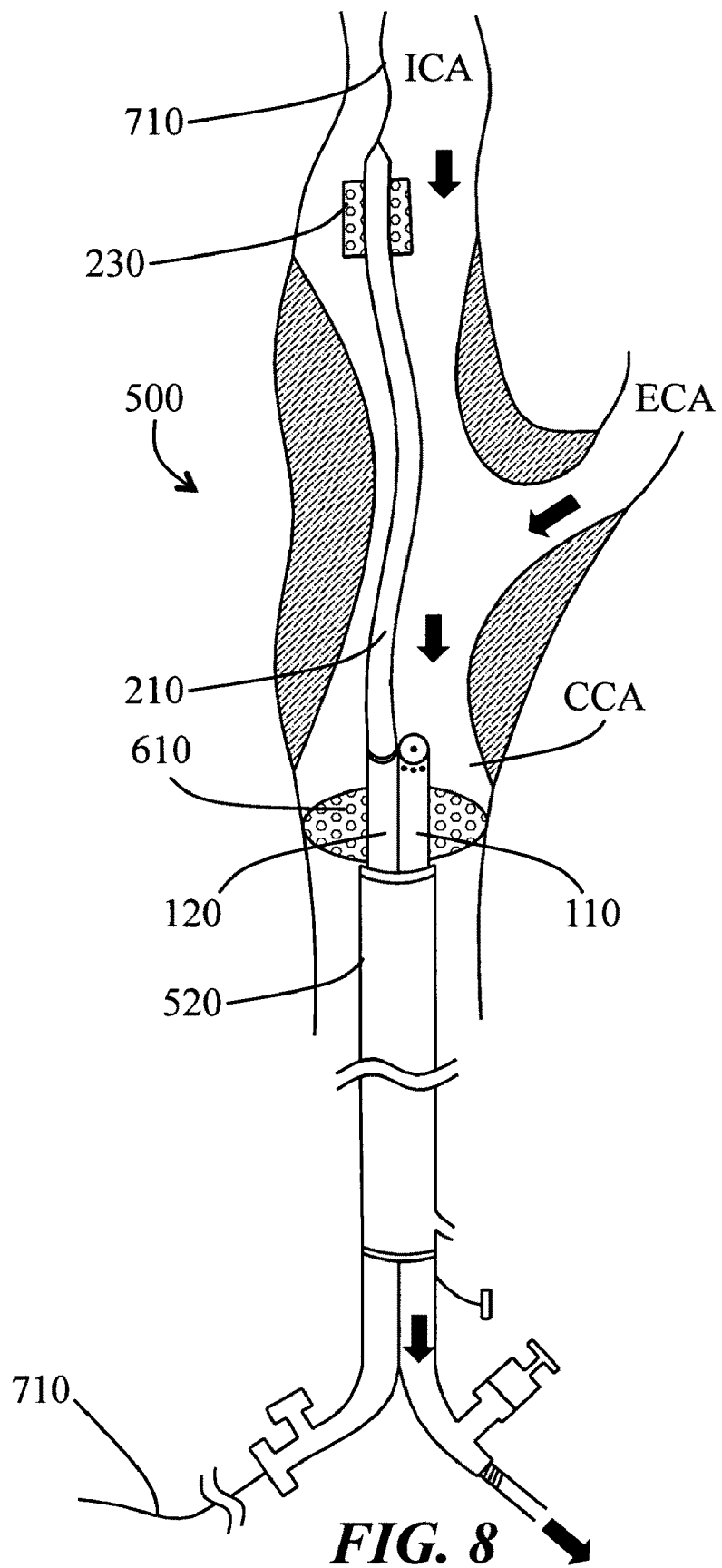
Figure 9:
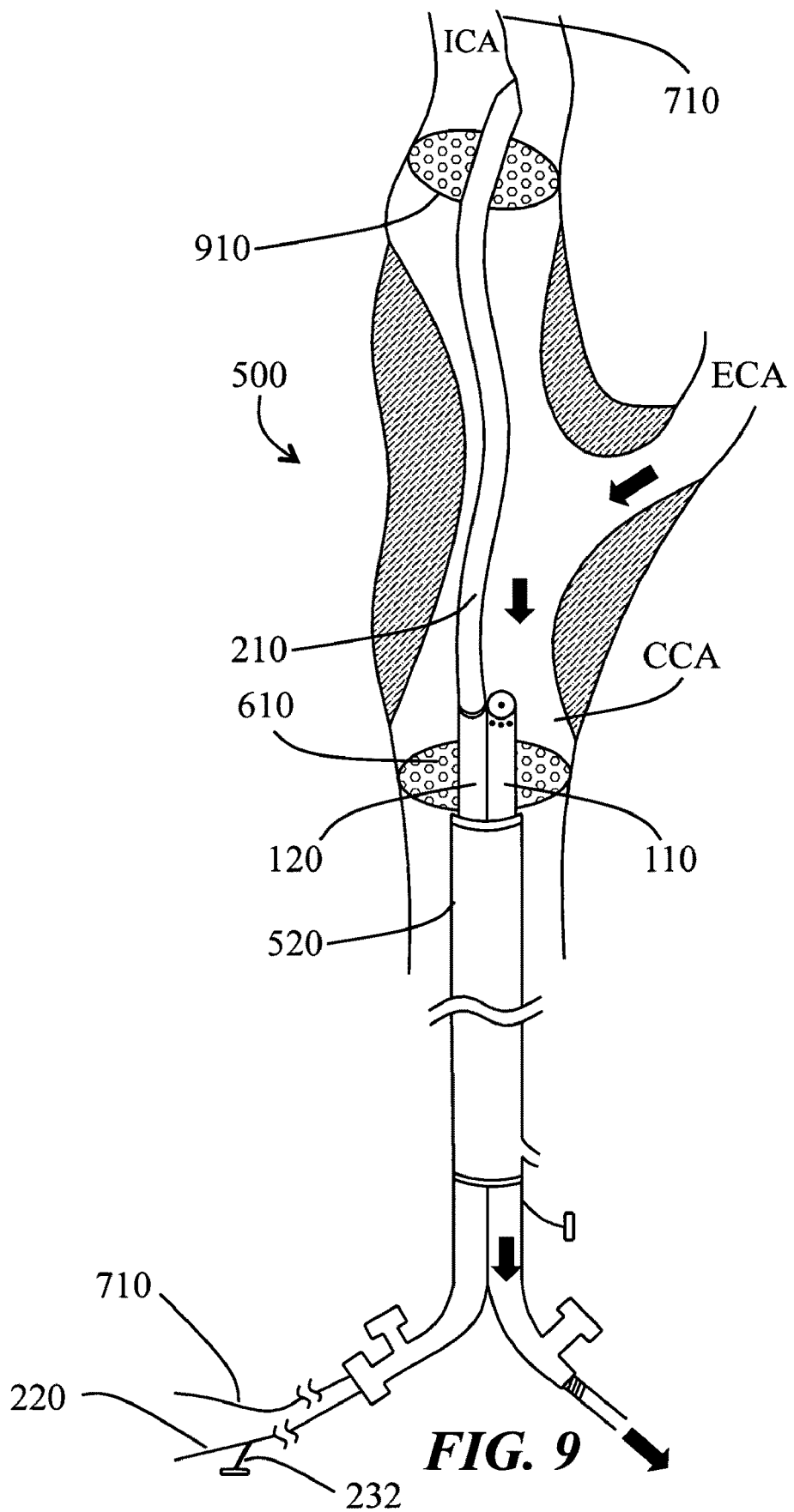
Figure 10:
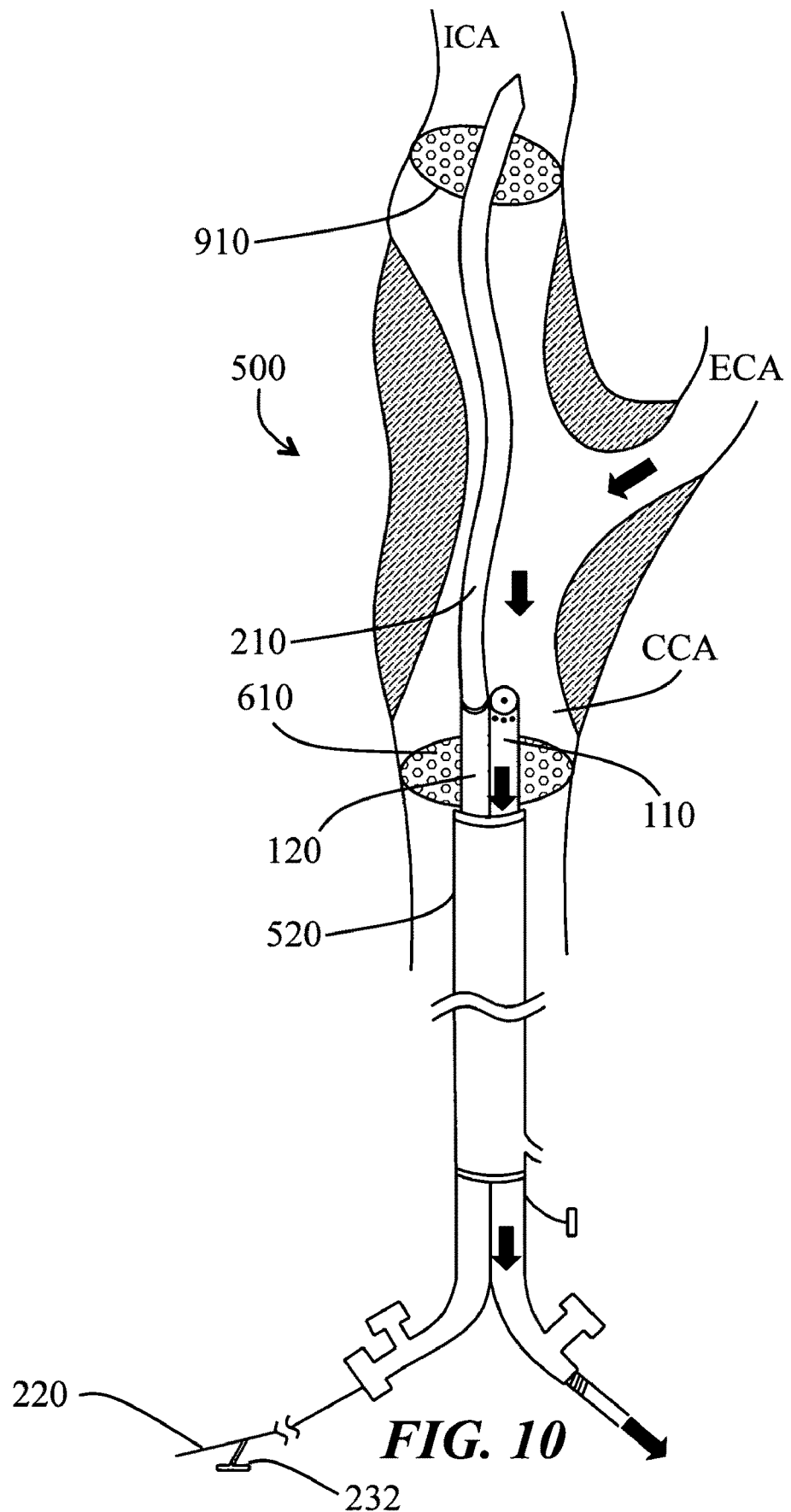

While maintaining aspiration of blood from first catheter 110, the distal balloon catheter 200 is advanced through the 0.014" guidewire 710 inside the lumen of second catheter 120 (FIG. 8). The second inflatable member 230 can be inflated 910 using inflation member 232 once it is advanced across the lesion as shown in FIG. 9. Upon inflation of second inflatable member 230, guidewire 710 can be removed (see FIG. 10 where 710 is removed). At this juncture, blood and debris if any inside the segment of vessel between the inflated members and from ECA will flow into the first catheter and out to the tubing and venous catheter.

Figure 11:
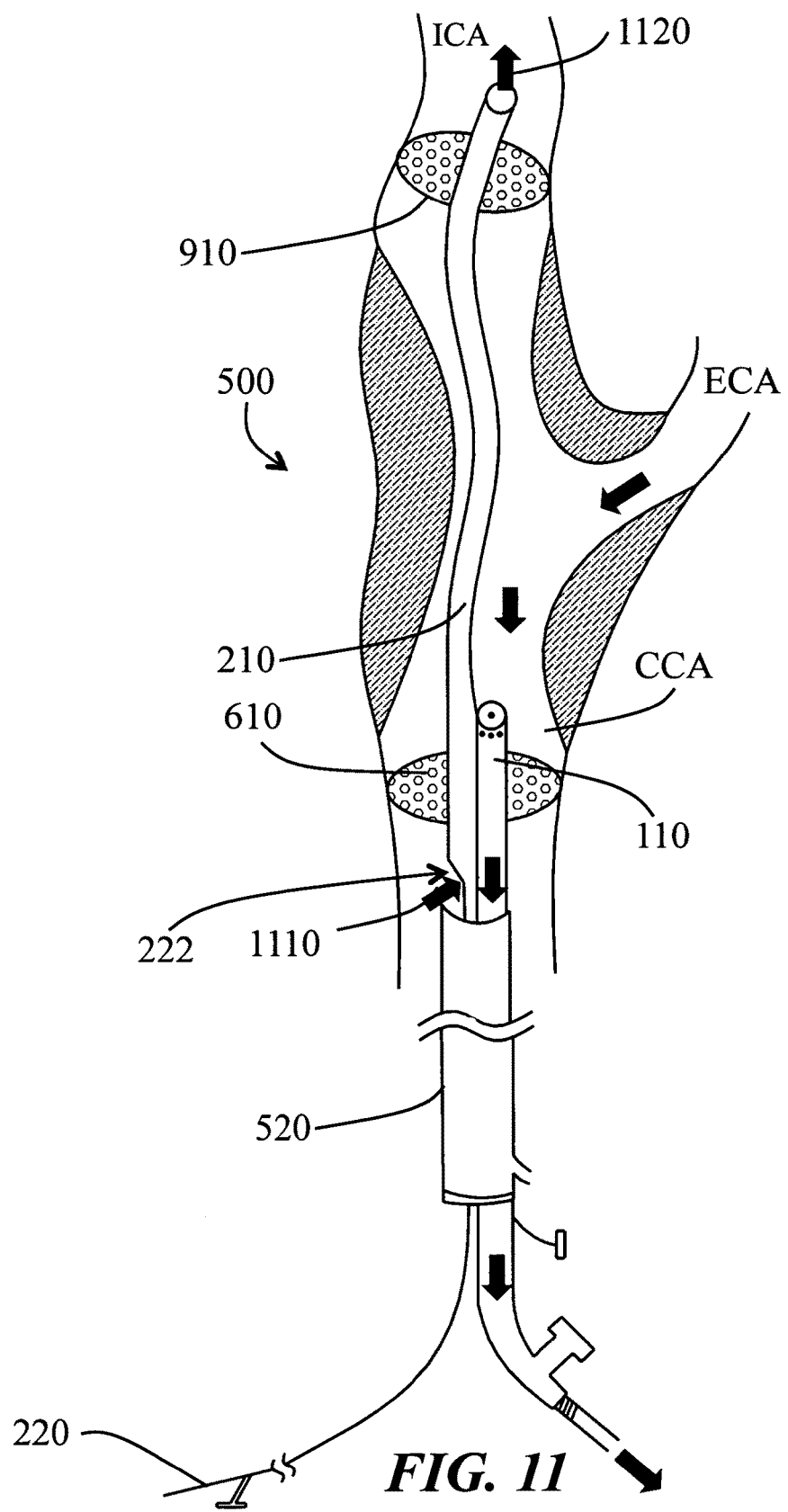
Figure 12:
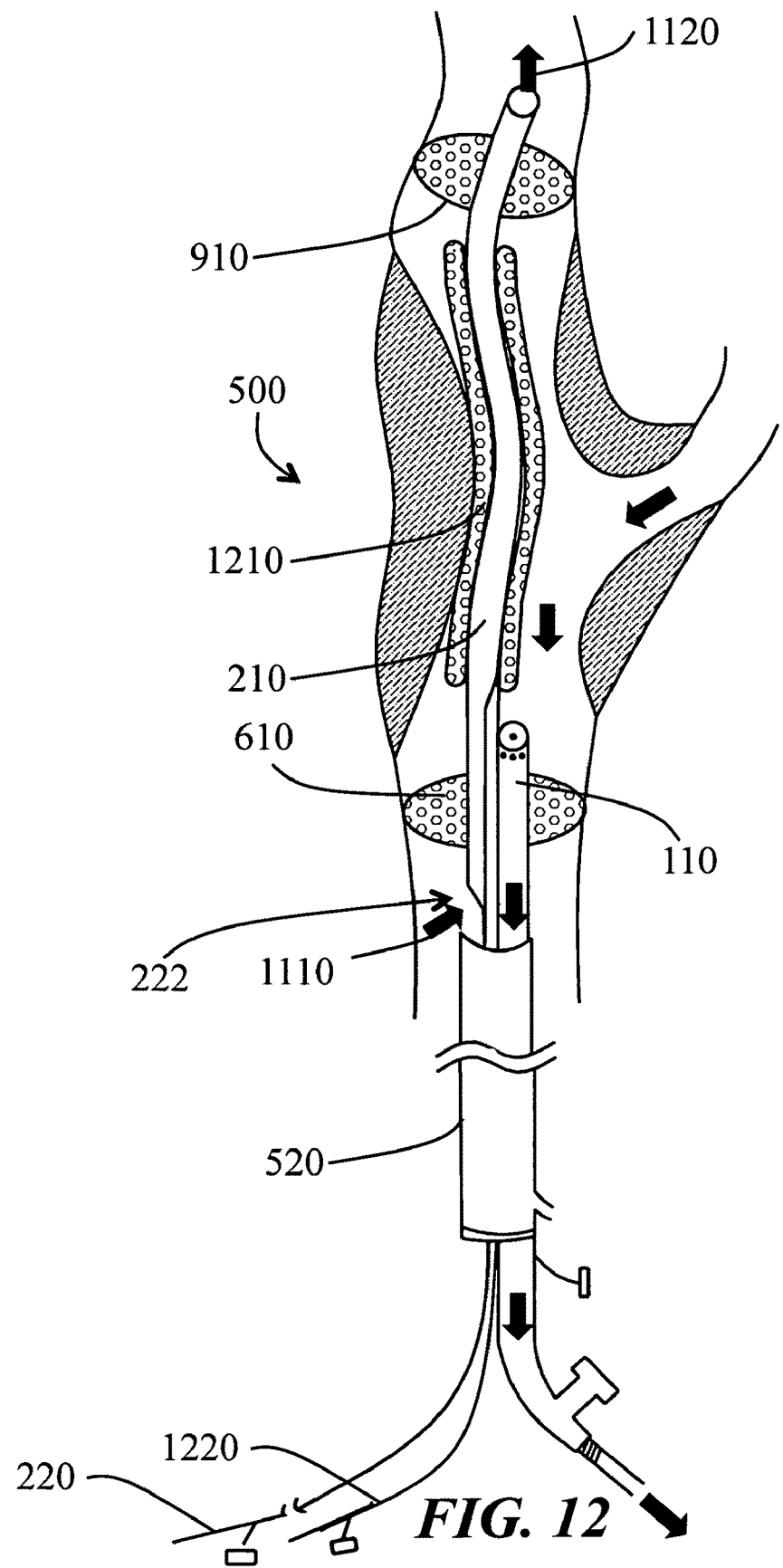
Figure 13:
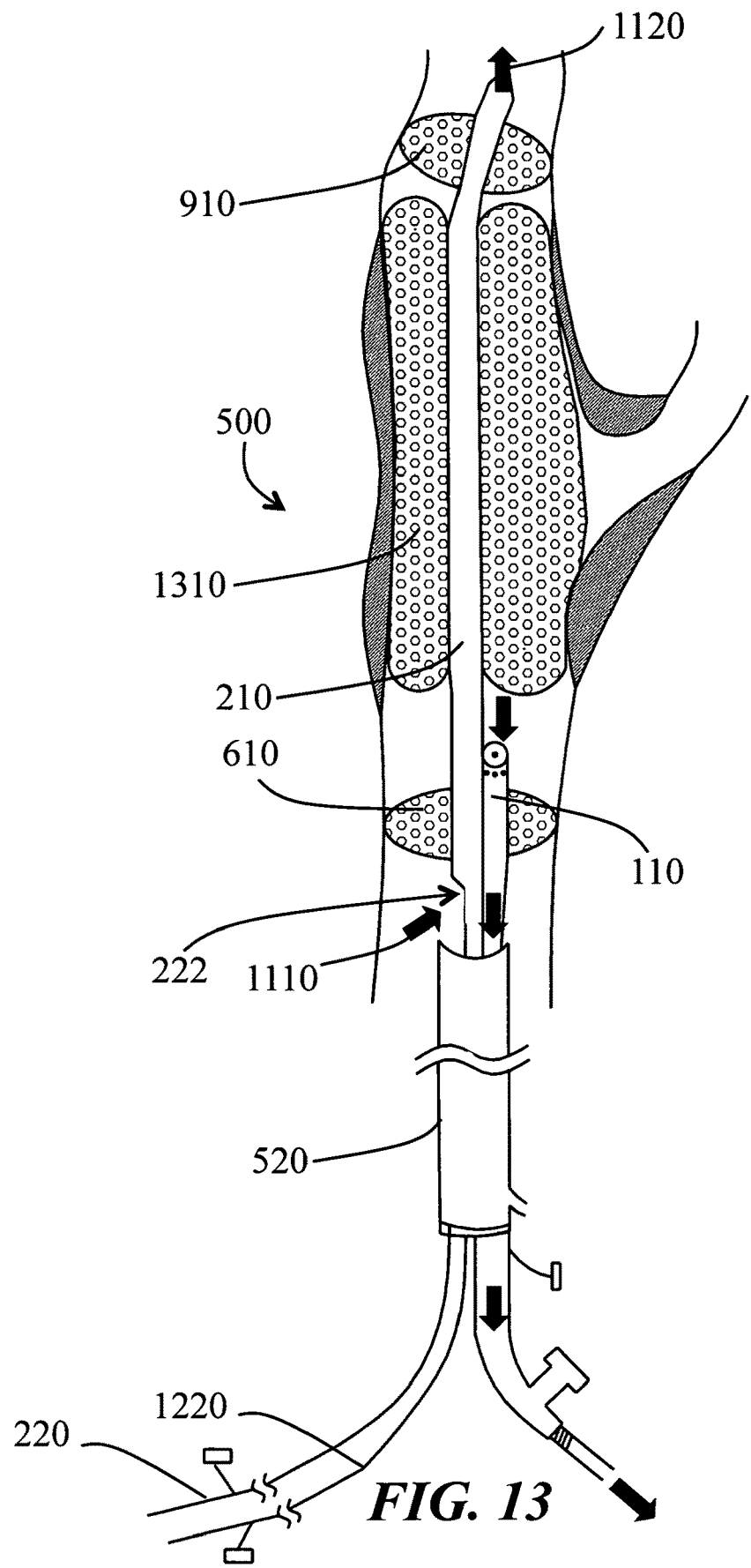
Figure 14:
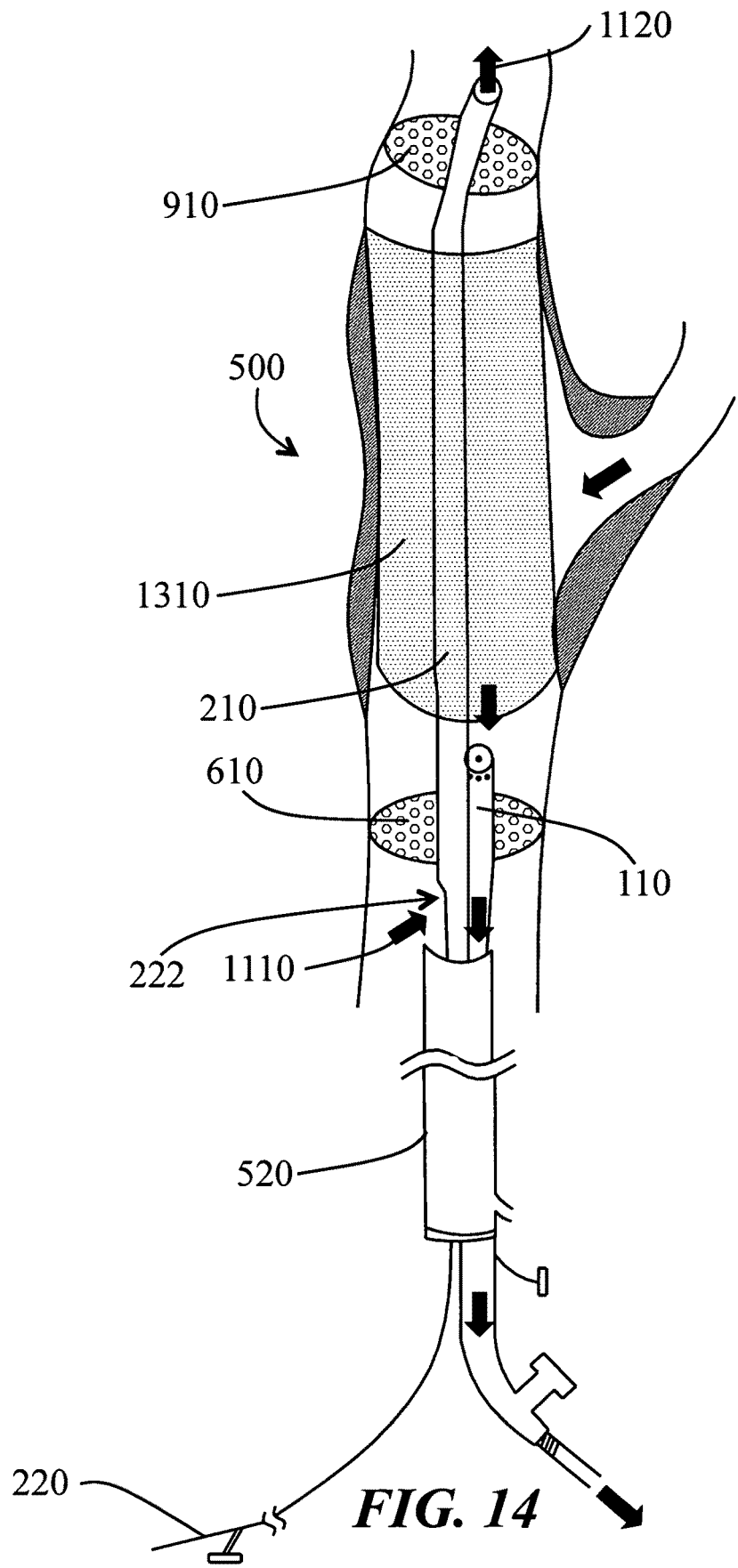

FIG. 11 shows where second catheter 120 is detached from first catheter 110 and removed. If necessary, the guiding sheath 520 can be pulled proximally to allow exposure of the proximal opening 222 of the catheter part 210 of distal balloon catheter 200 into the CCA proximal to the first inflated member 610. The catheter part 210 acts as an in-vivo shunt; blood will flow from the CCA proximal to the first inflated member 610 (through opening 222) to the ICA distal to the second inflated member 910 at this juncture. The flow direction is indicated from 1110 to 1120 and through catheter part 210. The compressible material 150 expands and fills up the space of the wall of second catheter to achieve water-tight effect FIG. 12 shows an angioplasty balloon 1210 pass up to the carotid lesion 500 over the outer surface of the proximal end and catheter part of the distal balloon catheter 200 210. Compressible material is compressed at this juncture. During and after balloon angioplasty and stent deployment 1310 (FIGS. 13 and 14; using angioplasty inflation member 1220), aspiration of blood or flushing of fluid over the segment of carotid artery being treated can be performed through side port of first catheter 110 (e.g. using port 114). A completion angiogram can be performed through first catheter 110 after the debris has been aspirated out.

Figure 15:
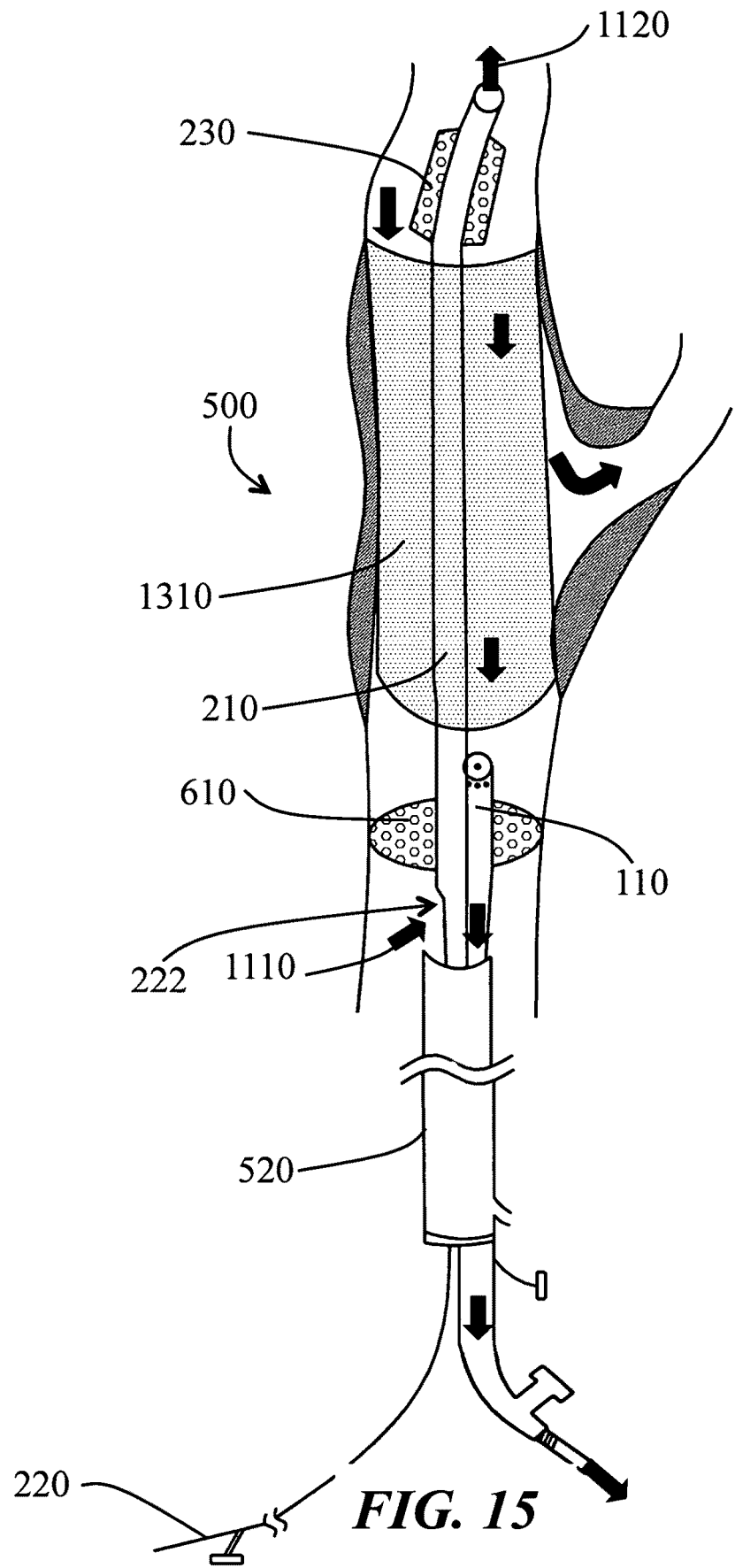
Figure 16:
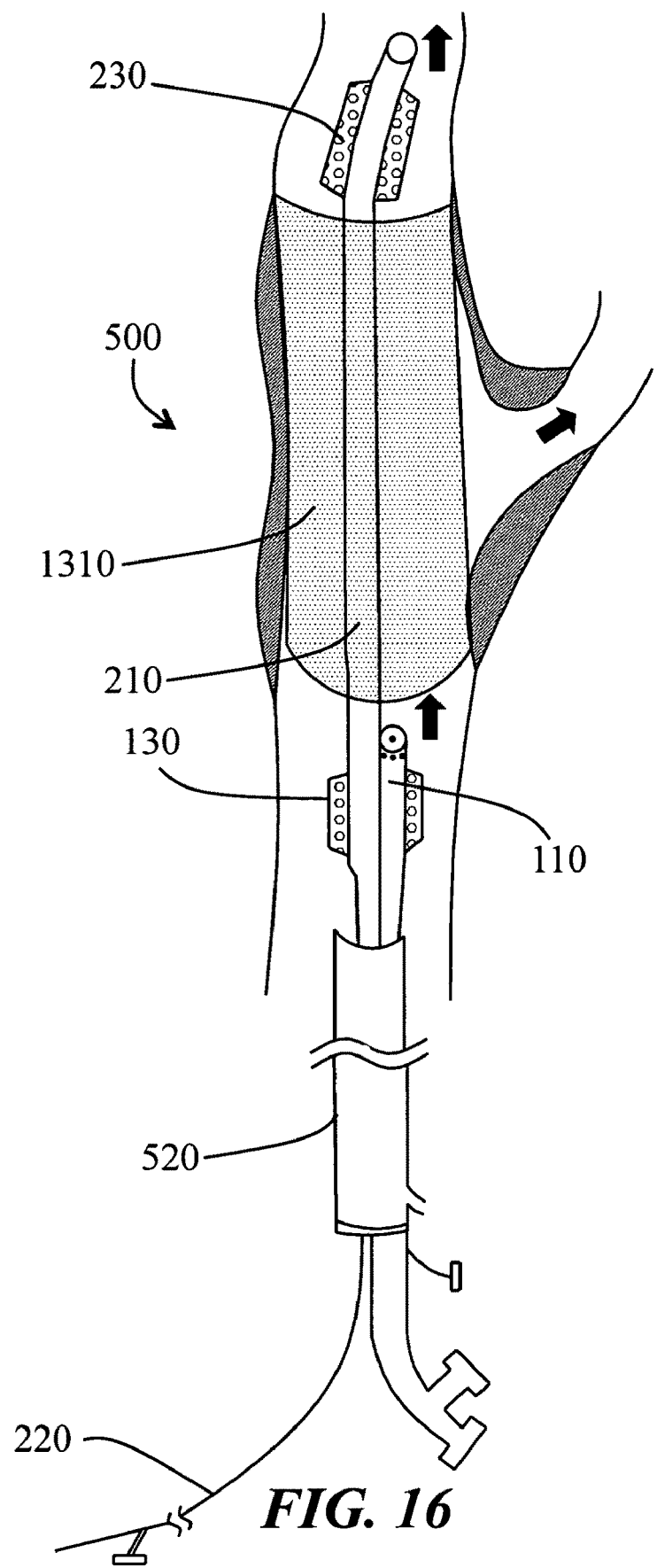

FIG. 15 shows deflation of the second inflatable member 230. With the in-vivo shunt functioning, blood will flow from the ICA to the ECA (see arrow in FIG. 15) and first catheter 110. In case there are still small amounts of debris inside the carotid bifurcation, they will flow into ECA or the first catheter. Once first inflatable member 130 has been deflated (see FIG. 16), forward flow of blood from the CCA to the ICA and ECA is re-established (see arrows in FIG. 16). The balloon catheter system or embolic protection system can then be retrieved and removed from the vessel.

Figure 17:
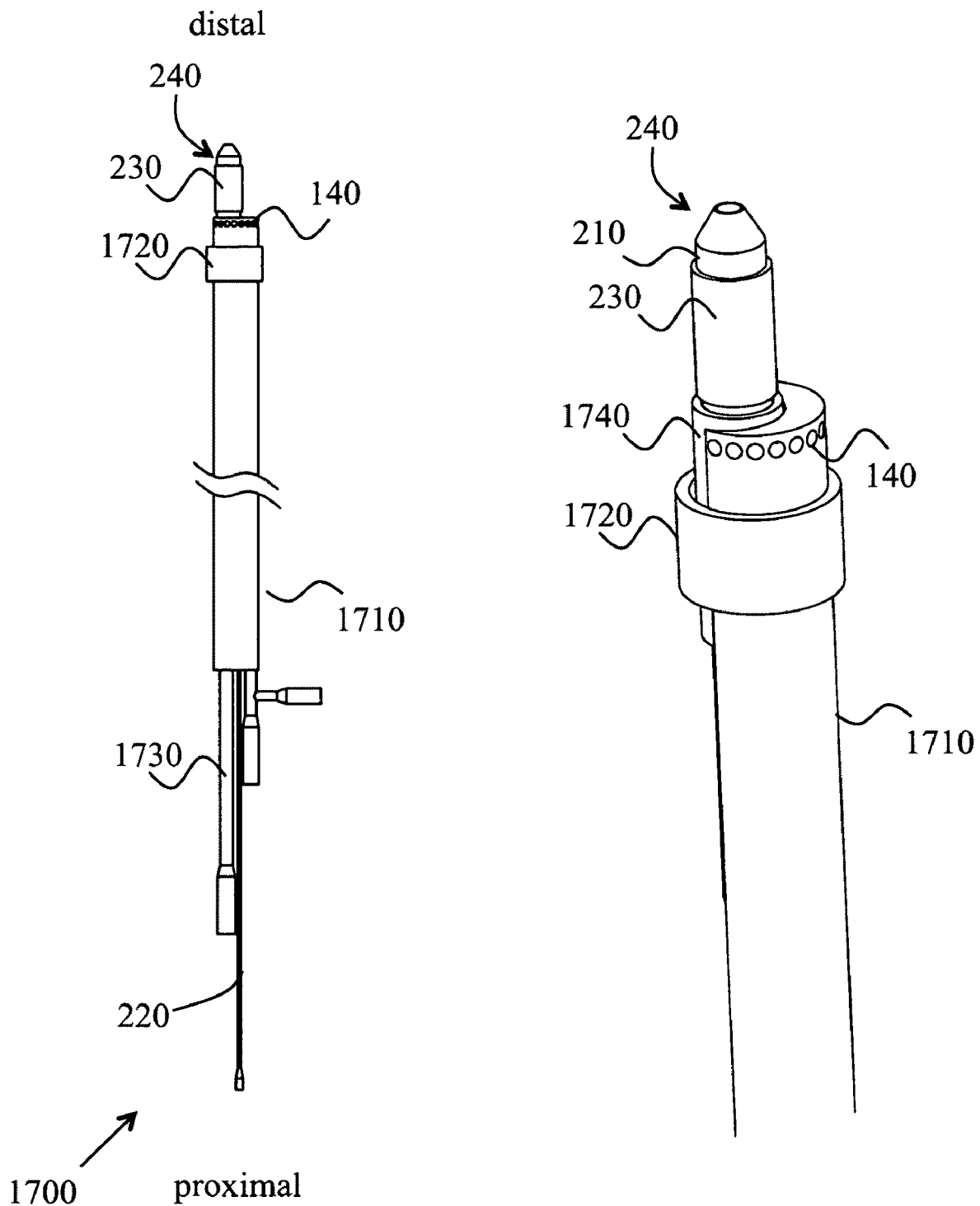
FIG. 17 shows according to an embodiment of the present invention a variation of the balloon catheter system (left) and a close-up of the distal part of this embodiment (right).
Figure 18:
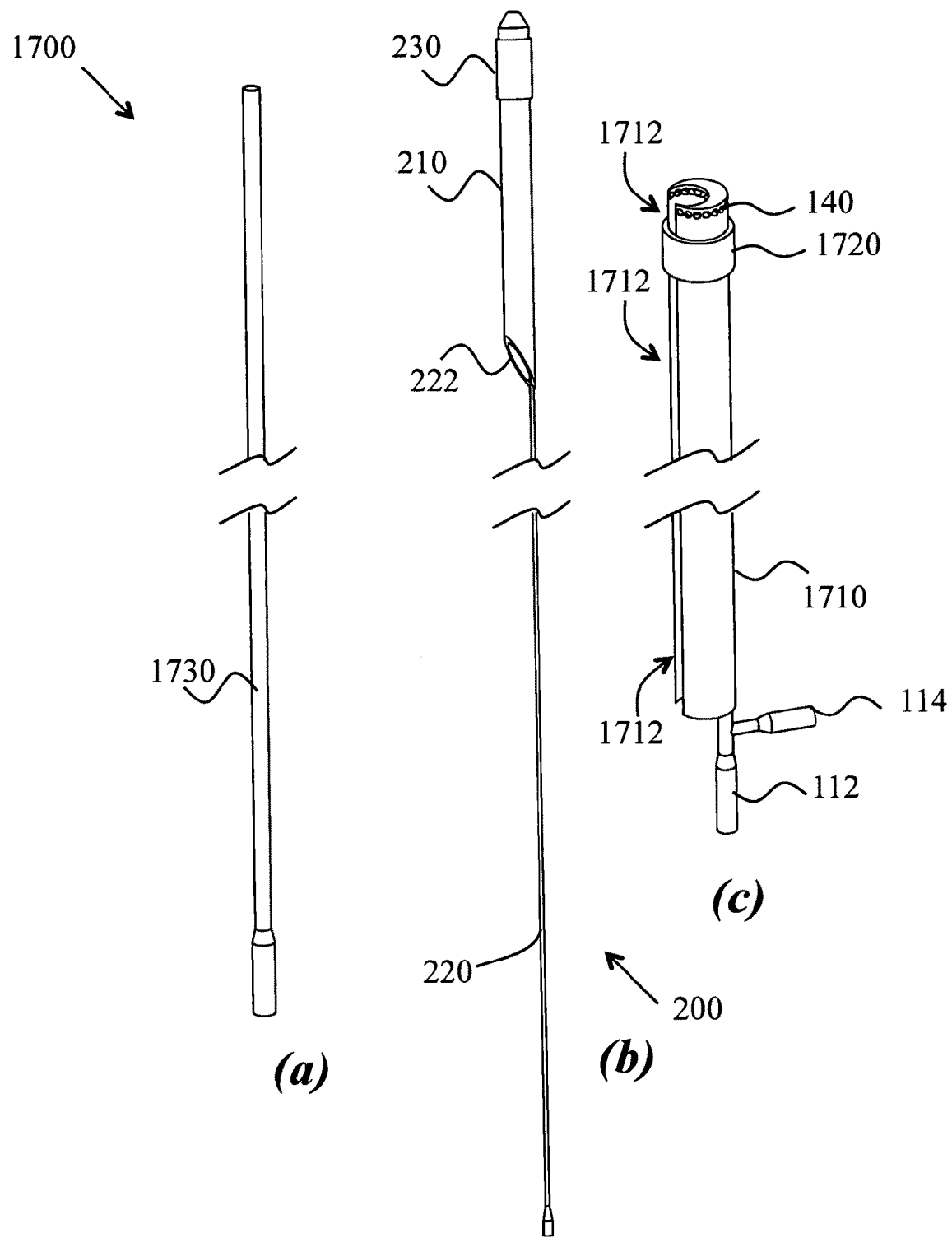
FIG. 18 shows according to an embodiment of the present invention a variation of the balloon catheter system (exploded view) with its three components, i.e. from left to right, a second catheter, a distal balloon catheter and a first catheter bearing proximal balloon.

As one of ordinary skill in the art will appreciate, various changes, substitutions, and alterations could be made or otherwise implemented without departing from the principles and methods of the present invention. For example regarding the balloon catheter system, balloon catheter system 1700, as shown in FIGS. 17-18, could have a first catheter 1710 bearing the proximal balloon that is semi-enclosed 1712 along its longitudinal axis and nearly crescent shape of its cross section to maximize surface area of the first catheter yet require a minimal increase in the total dimension of the device. First catheter 1710 has a first inflatable member 1720 encircling the outer diameter of first catheter 1710 and distal balloon catheter 200 near its distal end. Balloon catheter system 1700 further includes distal balloon catheter like 200 shown in FIG. 2, with the difference that second catheter 1730 is placed inside the lumen of the distal part 210 of distal balloon catheter 200 and the balloon bearing distal part 210 of the distal balloon catheter 200 is positioned more distal to the distal end of the first catheter 1710. A thin layer of compressible material 1740 surrounding but not attached to the catheter part 210 of the distal balloon catheter 200 proximal to the second inflatable member 230. The proximal exchange rod 220 of distal balloon catheter 200 is detachably connected to first catheter 1710 over their proximal part. Further in this embodiment, detachment of distal balloon catheter 200 from first catheter 1710 allows adjustment of the catheter part 210 of distal balloon catheter 200 inside the vessel as discussed supra. Furthermore, the second catheter 1730 can be removed from the distal balloon catheter so as to expose the proximal opening of the catheter part 222 of the distal balloon catheter and allow establishment of the in-vivo shunt 200. Accordingly, the scope of the invention should be determined by the following claims and their legal equivalents.

What is claimed is:

1. A balloon catheter system, comprising:
  (a) a proximal balloon catheter system, wherein said proximal balloon catheter system comprises:
    (i) a first catheter and a second catheter, wherein said first and second catheters are positioned side-by-side over at least part of the longitudinal area of their outer surfaces, wherein said first and second catheter are detachably connected to each other, and wherein said second catheter can be completely detached and removed from said catheter system during a procedure; and
    (ii) a first inflatable member attached to said first catheter near the distal end of said first catheter and, when said first and second catheters are positioned side-by-side, said first inflatable member encircling both the outer diameters of said first and second catheters; and
  (b) a distal balloon catheter distinguishing a catheter part with a distal end and a proximal end and an exchange rod attached to said proximal end of said catheter part, wherein the distal end of said catheter part of said distal balloon catheter has a conical tip of elastic material expandable under fluid or blood pressure, wherein said catheter part having attached thereto near its distal end a second inflatable member that encircles the outer diameter of said catheter part of said distal balloon catheter, wherein said catheter part of said distal balloon catheter, upon inflation of said first and second inflatable members of the balloon catheter system, is capable of acting as an in-vivo shunt to maintain blood flow from proximal of said first inflatable member to distal of said second inflatable member through said catheter part of said distal balloon catheter.

2. The balloon catheter system as set forth in claim 1, wherein at least said distal part of said distal balloon catheter can pass through the lumen of said second catheter of said proximal balloon catheter system and the position of said distal part of said distal balloon catheter can be adjusted via said exchange rod to position said second inflatable member with respect to said first inflatable member in a vessel.

3. The balloon catheter system as set forth in claim 1, wherein the distal end of said first catheter has side-openings distal of said first inflatable member.

4. The balloon catheter system as set forth in claim 1, wherein said first and second catheters each have at least one port near their proximal ends.

* * * * *